United States Patent [19]

Klotz, Jr. et al.

[11] Patent Number: 5,651,044
[45] Date of Patent: Jul. 22, 1997

[54] CAPACITIVE PROXIMITY DETECTOR FOR RADIATION IMAGER POSITION CONTROL

[75] Inventors: Theodore Henry Klotz, Jr., Scotia; Vivek Venugopal Badami, Niskayuna; Walter Whipple, III, Amsterdam; James Frederick Bedard, Schenectady; George Charles Goodman, Niskayuna, all of N.Y.

[73] Assignee: General Electric Company, Schenectady, N.Y.

[21] Appl. No.: 537,954

[22] Filed: Oct. 2, 1995

[51] Int. Cl.$^6$ ................................................. H05G 1/54
[52] U.S. Cl. ................................................. 378/117; 378/95
[58] Field of Search ........................ 378/91, 95, 117, 378/204; 340/540, 541, 561, 562

[56] References Cited

U.S. PATENT DOCUMENTS

| | | | |
|---|---|---|---|
| 4,127,775 | 11/1978 | Ohlson | 378/117 X |
| 4,320,766 | 3/1982 | Alihanka et al. | 128/671 |
| 5,019,804 | 5/1991 | Fraden | 340/562 |
| 5,097,495 | 3/1992 | Gray et al. | 378/117 |
| 5,105,455 | 4/1992 | Kato et al. | 378/117 |
| 5,486,700 | 1/1996 | Silberklang et al. | 250/363.04 |

OTHER PUBLICATIONS

Application entitled "Ultrasonic Ranging System for Radiation Imager Position Control," Ser. No. 08/537,576, filed Oct. 2, 1995.

Application entitled, "Imager Control System With Contact Detector," Ser. No. 08/537,580, filed Oct. 2, 1995.

*Primary Examiner*—David P. Porta
*Attorney, Agent, or Firm*—Donald S. Ingraham

[57] ABSTRACT

A capacitive proximity detection system for positioning a movable radiation imaging element support structure with respect to a subject includes a plurality of sensor plates disposed in a collar assembly around a portion of an imaging component disposed towards a subject; a multiplexer coupled to the plurality of capacitive plate elements and adapted to selectively electrically couple the sensor plate elements in one of a plurality of sensing range modalities; and a capacitive sensing processor coupled to the sensor plate elements via the multiplexer so as to detect proximity of object to the sensor plate as a function of the capacitance between the sensor plates and the subject. The imaging system typically further includes a shield system coupled to the multiplexer and disposed so as to focus the capacitive sensing of the sensor plate elements towards the subject. The shield system includes a plurality of shielding plate elements disposed in a shielding pattern that corresponds with the pattern of sensor plate elements in the collar assembly. The shield plate elements are coupled to the capacitive sensing processor to receive a shield plate feedback signal therefrom.

18 Claims, 3 Drawing Sheets

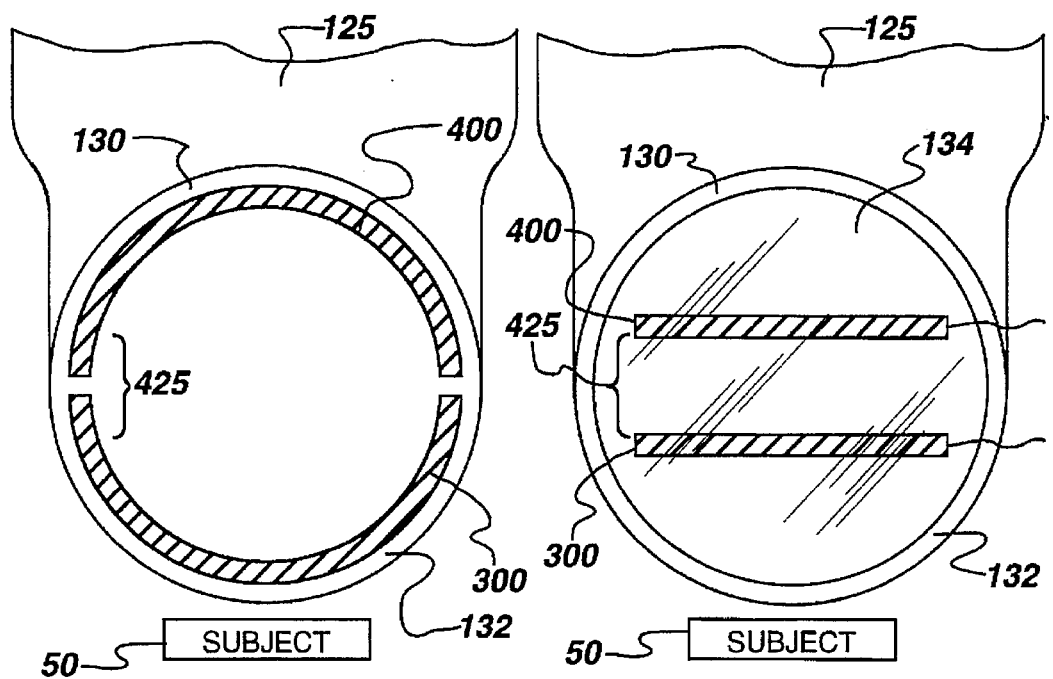
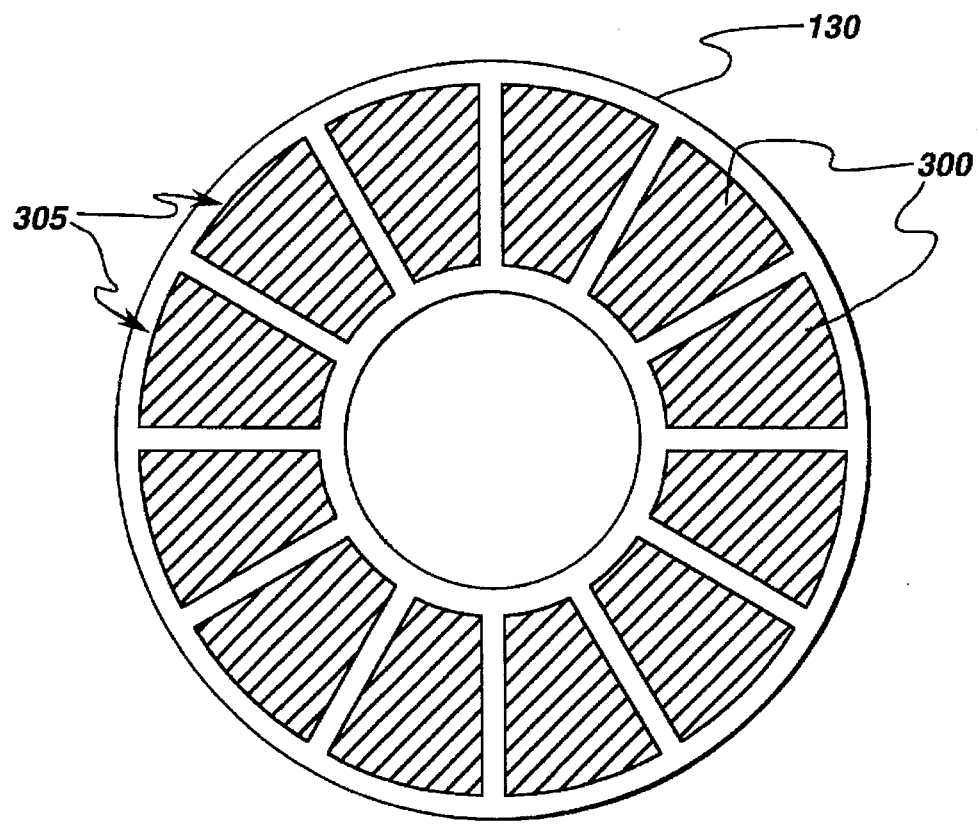

CAPACITIVE PROXIMITY DETECTOR FOR RADIATION IMAGER POSITION CONTROL

BACKGROUND OF THE INVENTION

This invention relates generally to radiation imaging devices and in particular to proximity measuring systems for determining the position of components of the radiation imaging system with respect to the subject of examination.

Medical radiation imagers, such as x-ray machines, must be accurately positioned close to the patient to provide the desired imaging information and such that components of the assembly do not physically collide with the patient. On some types of imaging equipment, such as computer tomography (CT) imagers or the like, a radiation detector, such as an x-ray image intensifier tube is positioned on a movable gantry arm opposite to another arm on which the x-ray source is disposed; the opposed arms can be swung 360° around a part of a patient's body, such as the head. It is desirable that the radiation detector be positioned close to (e.g., within about 1 inch) but not touch any part of the patient as the gantry arm rotates. In such systems an operator commonly controls the position of the radiation detector by means of manual control, such as with a joystick arrangement. The end of the radiation detector assembly nearest the patient is surrounded by a donut-shaped air-bag assembly. In what is commonly called "Level I" sensing, if the air-bag assembly comes in contact with the patient, a detected change in air pressure in the air-bag causes the control system to direct cessation of movement of the system. A pressure difference of about 0.3" of water is commonly used as the threshold to prompt a Level I stop. A second level of sensing, Level II sensing, refers to a situation when an additional 0.1" change (beyond Level I) in air-bag pressure occurs, such as from slight over-travel in the gantry arm after reaching the Level I shutdown point. A Level II signal causes a complete motor shutdown and locking of the gantry arms; the Level II motor control is accomplished via hard-wired relays outside of the normal computer-controlled gantry arm control circuits. After a Level II shutdown signal, the gantry arm assembly must be manually disengaged and hand-cranked away from the patient's body. This arrangement provides a dual-point failure mode in the sensing scheme. Most systems further have a contact switch disposed exterior to the air-bag that provides a further back up, such that physical contact resulting in activation of the contact micro-switches provides independent shutdown signals to the gantry arm control system.

Efficient and effective use of medical imaging equipment of this type is enhanced by operating modalities that follow the contour of the patient's body to maintain the radiation detector assembly at a desired separation from the nearest portion of the patient's body as the assembly is rotated around the body. It is desirable that no part of the radiation detector assembly and gantry arm come into contact with the patient's body at any time during the procedure, and further desirable that the control system be able to prevent contact with the patient and shutdown commands that are generated as a result of contact with the air-bag assembly disposed around the radiation detector.

SUMMARY OF THE INVENTION

A capacitive proximity detection system for positioning a movable imaging element support structure with respect to a subject of examination includes a plurality of capacitive sensor plate elements disposed in a sensor pattern; a multiplexer coupled to the plurality of sensor plate elements and adapted to selectively electrically couple the sensor plate elements in one of a plurality of sensing range modality switching units; and a capacitive sensing processing unit coupled to the sensor plate elements via the multiplexer so as to detect proximity of the subject to the sensor plate as a function of the capacitance between the sensor plate elements and the subject. The imaging system typically further includes a shield system coupled to the multiplexer and disposed so as to focus the capacitive sensing of the sensor plate elements towards the subject. The range sensing modalities include short range and long range modalities; in the shortest range modality, the multiplexer is adapted to couple sensor plate elements in a short range sensing modality switching unit, each switching unit comprising a single sensor plate element. In longer range sensing modalities, the multiplexer is adapted to couple sensor plate elements in a long range sensing modality switching unit, each long range switching unit comprising a plurality of sensor plate elements coupled together; the plates are typically electrically coupled in parallel, but alternatively can be coupled together in series.

The shield system includes a plurality of shielding plate elements that are coupled via the multiplexer to the capacitive sensing processor unit so as to receive respective shield feedback signals therefrom. The shielding plate elements are disposed in a shielding pattern that corresponds with the sensor pattern with the shielding plate elements being disposed between the sensor plate elements and the movable imaging element support structure in juxtaposition with a corresponding sensor plate element to form a plurality of paired sensor-shield plate sets.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like characters represent like parts throughout the drawings, and in which:

FIG. 3(A) is a cross-sectional view across one cylindrical segment of a collar assembly having a proximity detection system in accordance with one embodiment of this invention.

FIG. 3(B) is a cross-sectional view across one cylindrical segment of a collar assembly having a proximity detection system in accordance with another embodiment of this invention.

FIG. 3(C) is an equatorial cross-sectional view across a collar assembly having a proximity detection system in accordance with this invention.

DETAILED DESCRIPTION OF THE INVENTION

Figure 1:
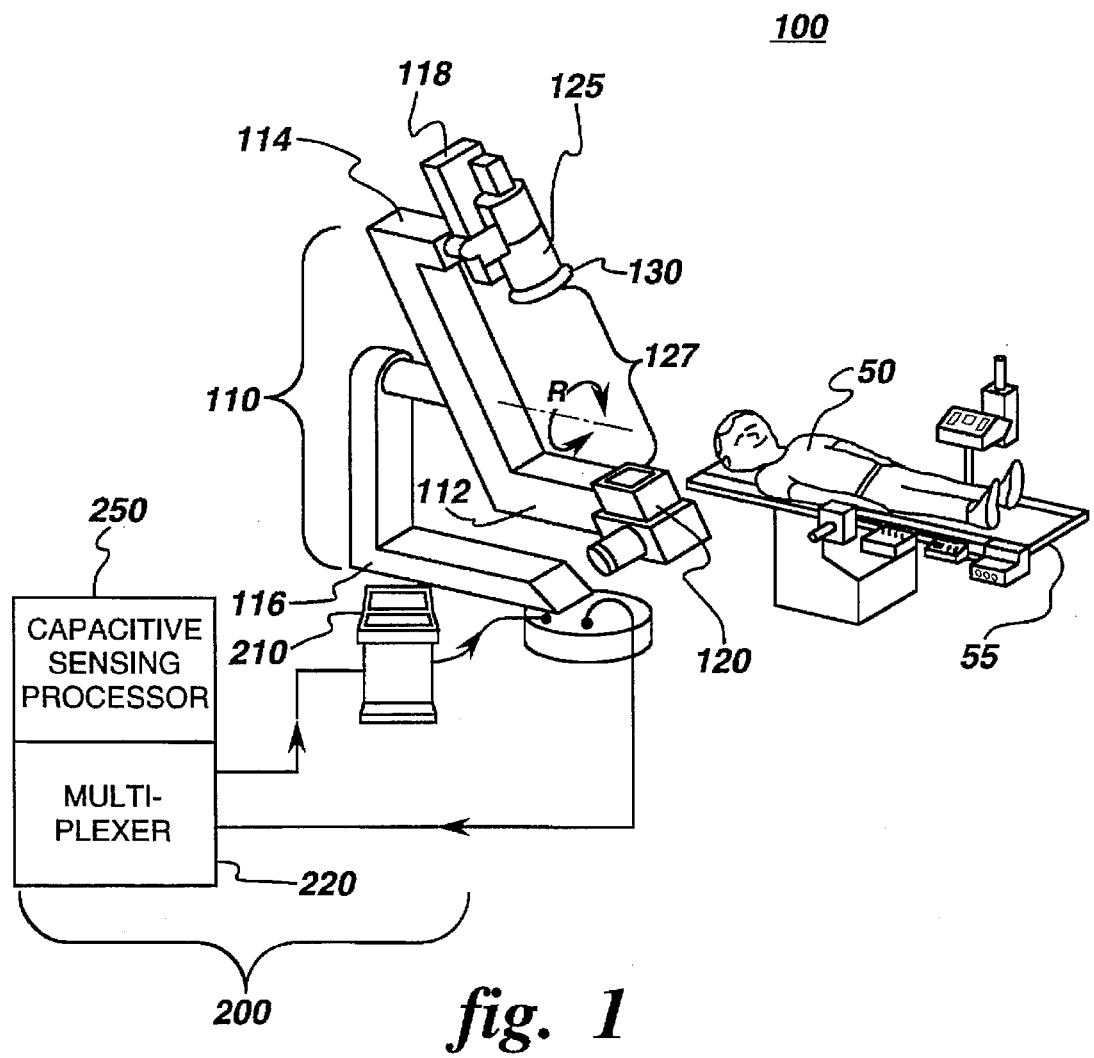
FIG. 1 is a part perspective and part block diagram of a radiation imaging system in accordance with this invention.

A radiation imaging system 100 comprises a movable gantry assembly 110 that is coupled to an imager control system 200 (FIG. 1). Control system 200 typically comprises an operator console 210 for commanding respective modalities of operation of imaging system 100, a multiplexer 220, and a capacitive sensing processing unit 250. Control system 200 generates control signals corresponding to the proximity of components on gantry assembly 110 to the object being imaged so as to move gantry assembly 110 to a desired position with respect to the imaged object.

Gantry assembly 110 comprises a first arm 112 and a second arm 114 that provide a support structure for components of the radiation imaging system. Typically a radiation source 120 (such as an x-ray source or the like) is mounted on first arm 112 and radiation detector assembly 125, such as an x-ray image-intensifier tube (II-tube), is mounted on second arm 114 so as to be disposed opposite radiation source 120 across an intervening imaging region 127.

By way of example and not limitation, as presented herein radiation imaging system 100 is adapted for medical imaging of a patient's body; alternatively, the proximity detection system of this invention can be used with other types of radiation imaging, such as is used in industrial processes for quality control and the like (e.g., non-destructive testing). Typically the object of study, or a subject 50, is a portion of a patient's body, such as the patient's head, that is resting on an examining table 55. Gantry arms 112 and 114 are rotatably mounted on a gantry foundation 116 so that they can be rotated around subject 50, e.g., as indicated by the arrow "R" in FIG. 1. Radiation detector 125 is further mounted on a movable slide 118 so that it can be disposed closer to or farther from radiation source 120, thus respectively decreasing or increasing the extent (or length between the source and detector components) of imaging region 127. Gantry assembly 110 and movable components thereon, such as slide 118, are typically driven by drive systems (not shown), such as an electrical motor and transmission, that are responsive to signals from control system 200.

When initially positioning the patient within imaging region 127, slide 118 is positioned to provide a large extent of imaging region 127; during the x-ray examination procedure, however, it is desirable that radiation detector 125 be positioned in close proximity to subject 50, but not in physical contact with the subject. A collar assembly 130 is typically disposed around the end or portion of II tube 125 that is closest to the surface of subject 50. Collar assembly 130 is typically donut-shaped, that is, having a circular tube-type structure.

In accordance with this invention, capacitive proximity detection system 200 (FIG. 2) comprises multiplexer 220 that is coupled to capacitive sensing processing unit (or processor) 250, and typically further comprises a shield system 400 coupled to multiplexer 220 and processor 250. Capacitive proximity detection system 200 is coupled to components of radiation imaging system 100 so as to sense the position of radiation detector assembly 125 (FIG. 1 ) with respect to subject 50 and to generate signals to control the movement of gantry assembly 110 and components thereon (such as movable slide 118) to dispose radiation detector 125 in a desired location with respect to subject 50. Typically proximity detection system 200 provides accurate and contemporaneous proximity sensing sensitivity so that signals can be generated by control console 210 to position movable slide 118 (and thus radiation detector 125) automatically during an imaging process as gantry assembly 110 rotates around subject 50, thus reducing the time and inaccuracy associated with manual positioning of the gantry arm assembly with respect to subject 50 during an imaging process. The precise ranging information of the system is further valuable in semiautomatic, or operator-controlled motion of the imaging apparatus, such as would be used when the operator needed a more detailed or directional view of a specific portion of subject 50.

Further, in accordance with this invention, capacitive proximity sensing system 200 comprises a plurality of sensor plate elements 300 that are disposed around collar assembly 130, as illustrated in FIGS. 3(A)–3(C), and that are coupled to multiplexer 220 so as to be selectively coupled together in one of a plurality of sensing range modality switching units. The sensitivity of proximity sensing system 200 corresponds to the area of electrically sensitive (or responsive) sensor plate elements 300 (that is, the area of plates that are electrically coupled together so as to electrically comprise the functional equivalent of a single plate) and the area of the subject being sensed. For example, for a flat parallelogram shaped sensor plate having an area of about 5 $cm^2$, a change in capacitance can be detected with respect to a subject planar surface (the respective planar surfaces being oriented substantially parallel to one another and separated by air or similar dielectric material) at a separation distance between the planar surfaces of about 5 cm. As the lateral separation distance decreases, corresponding changes in capacitance occur that can provide an accurate indication of the proximity to the subject. Developing an output signal that accurately corresponds to the distance to a subject becomes more problematic for a non-planar subject at close ranges, such as a human body with appendages such as nose, ears, limbs, and the like. Accurate ranging to a contoured surface requires that the area of the capacitive sensor approximately correspond to (e.g., have a size 50% or greater of the size of) a portion of the surface area of the subject roughly disposed parallel to the plane of the sensor. Thus, for example, accurately detecting the presence and location of a nose on the head of a person undergoing examination requires that the capacitive detecting sensor be of sufficiently small area, that is, have an area corresponding to the area of the nose, so as to be able to develop an unambiguous range signal attributable to the capacitive effect resulting from proximity to the nose.

Each sensor plate element 300 comprises a conductive material (e.g., aluminum, copper, conductive carbon compounds, or the like) having an area that is selected in the design process so that capacitive proximity sensing system 200 can provide a desired distance-sensing sensitivity. For a system 200 adapted for use in sensing human anatomy, such as is used in an x-ray imager, the area of each sensor plate element is typically in the range between about 1 $cm^2$ and 15 $cm^2$. Sensor plates 300 are typically disposed in the interior of the circular tube-like structure of collar assembly 130; collar assembly 130 comprises a surface structure 132 comprising a pliable material, such as rubber or soft plastic (in use, commonly a sterile covering of plastic or the like is disposed across the collar assembly to protect against spread of infection in the event of inadvertent contact of collar assembly with a patient).

In one embodiment of the present invention, sensor plates 300 are disposed so as to be conformal with (that is, conform to the shape of) the curved surface structure 132 of the tube-like collar assembly 130, as illustrated in the cross-sectional view of FIG. 3(A) (that is, cut across one portion of the tube-type structure of the donut-shaped collar assembly). Such a structure can be readily fabricated by the deposition and patterning of conductive material on the interior side of curved surface structure 132. An alternative embodiment is illustrated in the cross-sectional view illustrated in FIG. 3(B) (illustrating an equivalent view of collar assembly as FIG. 3(A)), in which sensor plates 300 are disposed within the interior of collar assembly 130 and are suspended in a dielectric material 134 such as polyimide, foam rubber, or the like. In this alternative embodiment, sensor plates are oriented so that the plane of the plates is substantially perpendicular to the lateral axis of the collar assembly, that is, the axis corresponding to the path of the radiation beam dispensed by the radiation source.

Sensor plate elements 300 are disposed around collar assembly in a sensing pattern 305 as illustrated in FIG. 3(C) (a cross-sectional view of one-half of the donut-shaped collar assembly cut along an equatorial plane). The sensing pattern is selected such that sensor plate elements 300 extend circumferentially, typically at equiangular intervals, over a large portion of the collar assembly area so that the proximity detection system can provide long range detection of an object; localization of a subject with respect to a segment on collar assembly 130; and sensitive short range measurement of the position of the subject with respect to the collar assembly. The size of individual sensor plates and the total number of plates are selected in the design process as noted above; by way of example and not limitation, a collar assembly 130 used in an x-ray imager applications may have an outer diameter in the range of about 10 cm to about 40 cm, and may have between about 4 and 75 sensor plates 300 disposed therein, which plates may have a respective area in the range between about 1 $cm^2$ (e.g., an arrangement with many (e.g., 64) sensor plates) and 100 $cm^2$ (as might be found in an arrangement with few (e.g., 4) plates).

Each sensor plate is respectively electrically coupled via multiplexer 220 to capacitive sensing processor 250 to enable electrical signals corresponding to the proximity of subject 50 to individual sensor plates 300 to be processed. Multiplexer 220 comprises switching circuits 225 (comprising, for example, rotary switches, semiconductor integrated circuit multiplexers, or the like) that selectively couple sensing modality switching units to processor 250. Processor 250 comprises a range sensing modality selector 251 coupled to multiplexer 220 so as to control switching circuits 225 to couple together respective sensor plate elements in respective sensing modality switching units. Dependent on the detection range desired for proximity detection system 200, a sensing modality switching unit may comprise a single sensor plate element 300, or, alternatively, a plurality of sensor plate elements 300 coupled together in series or parallel. Commonly, multiple plates are coupled together in parallel so as to reduce electrical resistance.

Figure 2:
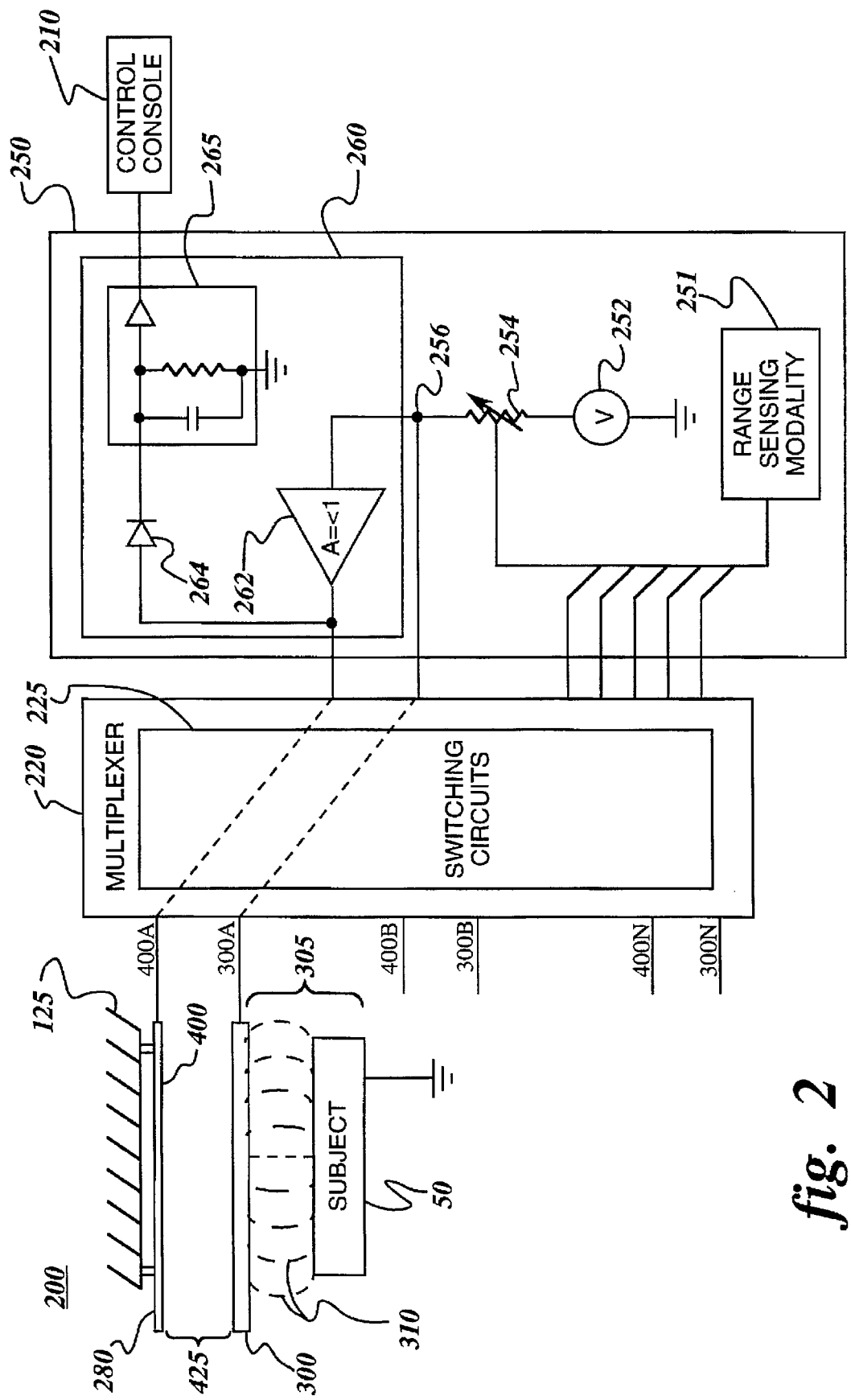
FIG. 2 is a schematic of a proximity detection system in accordance with this invention.

Commonly, the shortest range operating modality of capacitive sensing system 200 provides for each sensing modality switching unit to comprise a single sensor plate element 300; intermediate range operating modalities provide for at least two sensor plate elements to be electrically coupled together so as to electrically comprise one larger size sensor plate with respect to processor 250, and so forth, with progressively larger number of sensor plate elements 300 being electrically coupled together to form respective range sensing modality switching units, each of which has a respective sensitivity for detecting a subject having a planar component at a respective distance from collar assembly 130. For example, as illustrated in FIG. 2, capacitive sensing system 200 may comprise sensor plate elements $300_A$–$300_N$ (this nomenclature is used to denote any number of sensor plate elements); respective short range sensing modality switching units (having the greatest short range sensitivity) comprise individual sensor plate elements $300_A$–$300_N$ respectively individually coupled to processor 250 via switching circuits 225 so that the capacitance with respect to each individual sensor plate element is determined. An intermediate range sensing modality switching unit may comprise, for example, sets of multiple sensor plate elements coupled together, for example, plate elements $300_A$ through $300_C$ coupled together, $300_D$ through $300_F$ coupled together, and so forth. Sensor plate elements in a sensing modality switching unit are coupled together and thence to processor 250. The longest range sensing modality switching unit would comprise sensor plate elements $300_A$–$300_N$ coupled together and thence to processor 250 (thus forming effectively one large sensor plate and providing a sensing system having the long range but with reduced resolution with respect to the shorter range switching modalities).

Processor 250 further comprises a range sensing modality selector 251 that is coupled to control switching circuits 225 so as to selectively couple respective sensing range modality switching units to processor 250 so as to time multiplex the various sensing range modality switching units with processor 250. Range sensing modality selector thus enables multiplexer 220 to scan the respective sensing modality switching units (time multiplexing the capacitive sensing) so that objects in proximity to each of the respective sensing modality switching units can be detected by processor 250.

Processor 250 further comprises means for sensing a change in capacitance between the sensor plate element or elements 300 in a respective sensing range modality switching unit and the subject 50. By way of example and not limitation, the capacitance sensing circuit of processor 250 as illustrated in FIG. 2 comprises a signal generator 252 coupled to the sensor plates in a given sensing range modality switching unit (for ease of discussion a single sensor plate $300_A$ will be used to illustrate the operation of the circuit) via a variable resistor 254 (resistance is varied by range sensing modality unit 251 for impedance matching purposes in different sensing range modality switching units (e.g., higher resistance with smaller numbers of sensors coupled together). The amount of voltage drop across resistor 254 will be a function of the amount of voltage drop across an effective capacitor 305 formed between sensor plate $300_A$ and subject 50; dependent on the proximity of subject 50 to sensor plate $300_A$, the voltage drop across electrical field 310 (representative lines of which are illustrated in phantom in FIG. 2) between the capacitor plates will change. Measurement of the voltage at a junction 256 in this embodiment is accomplished with a high impedance amplifier circuit 260. Alternatively, other available capacitance detection systems, such frequency-based capacitance measurement, e.g. a Theremin oscillator (inductance-capacitance (LC) loop type), or the like, can be adapted to provide capacitance sensing for processor 250.

In accordance with this invention, proximity sensing system 200 typically further comprises a shield system having a plurality of shielding plate (or guard plate) elements 400 that are disposed in collar assembly 130 (FIG. 3(A) and 3(B)). The shield (or guard) plate elements 400 are disposed on a portion of collar assembly 130 that is between the sensor plate elements 300 and radiation detector assembly 125 and movable slide 118 so as to focus the capacitive sensing of sensor plate elements 300 towards imaging region 127 (FIG. 1) As used herein, "focus" refers to electrically effecting the proximity sensing system so that the variable capacitance sensed by the system corresponds to the capacitance between sensor plate element 300 and subject 50 in the imaging region 127 as opposed to the capacitance between sensor plate element 300 and the components mounted on gantry 110, such as radiation detector assembly 125.

Shielding plate elements $400_A$–$400_N$ (FIG. 2) (this nomenclature is used to indicate any number of shielding plate elements) are disposed in collar assembly 130 in a shielding pattern that corresponds with sensing pattern 305

(FIGS. 3(A) and 3(B)). Typically, the number of shield plate elements 400 in collar assembly 130 is the same as the number of sensor plate elements 300, and shield plate elements 400 are positioned in collar assembly so as to form a plurality of paired sensor-shield plate sets 425 (FIG. 3(B)). In each paired sensor-shield plate set, the respective shield and sensor plate elements in a paired set 425 are disposed opposite one another in collar assembly 130, with the shield plate being disposed between the sensor plate and gantry assembly components such as radiation detector assembly 125. For example, as illustrated in FIG. 2, sensor plate element $300_A$ is disposed in a paired set 425 with shield plate element $400_A$. Shield plate elements typically are similar in all respects of construction to sensor plate elements, as noted above. For example, shield plate elements 400 can be disposed conformably along the upper surface of collar assembly 130 as illustrated in FIG. 3(A), or alternatively, disposed within collar assembly 130 as illustrated in FIG. 3(B).

Shield plate elements $400_A$–$400_N$ are electrically coupled to proximity sensing system processor 250 via multiplexer 220 (FIG. 2). Each shield plate element 400 is coupled via multiplexer 220 to high impedance amplifier circuit 260 so as to receive a shield (or guard) plate feedback signal therefrom. Amplifier 260 is adapted to generate respective shield plate feedback signals for each sensing modality switching unit, that is, one shield plate feedback signal is applied to the respective shield plate elements for each paired sensor-shield plate set that is coupled together via multiplexer 220 for capacitive proximity sensing system 200. Alternatively, multiple amplifiers can be used for generating respective shield feedback signals.

As illustrated in FIG. 2, high impedance amplifier circuit 260 comprises an attenuating amplifier 262 (that is, one with a gain less than unity) that is coupled to resistor 254 such that the input signal for attenuating amplifier 262 corresponds to the voltage at junction 256. The output of attenuating amplifier comprises the shield plate feedback signal that is coupled to shield plate element 400 via multiplexer 220. As shield plate feedback signal is attenuated through amplifier 262, the respective shield plate element 400 and sensor plate element 300 in each paired set 425 do not oscillate together; instead, the shield plate element, with shield plate feedback signal applied, has the effect of focusing (that is, directing the electric field of) the proximity sensing system towards imaging area 127 (FIG. 1) because the shield plate elements 400 shield or guard the sensor plate elements 400 from electrically detecting the presence of radiation detector assembly 125 and other items mounted on gantry assembly 110.

High impedance amplifier circuit 260 further comprises means such as a peak detector circuit to generate a range signal. For example, a diode 264 is disposed to couple the output of attenuating amplifier 262 to a resistance-capacitance (R-C) loop 265 that serves to provide a range signal that corresponds with the variable capacitance between the respective sensor plates 300 (individually or as coupled together in respective sensing modality switching units) and the subject. RC loop 265 is typically coupled to control console 210 to provide the processor output range signal; the range signal is further processed to control the motion of gantry arm 110 and components on the arm, such as movable slide 118.

In operation, a patient is positioned on examining table 55 and imaging system 100 is commanded from control console 210 to commence the imaging process. Gantry arm 110 is positioned so as to dispose radiation detector assembly 125 in close proximity to the portion of the patient to be examined, e.g., the patient's head. Capacitive proximity sensing system initially selects a long-range sensing modality, such as having all sensor plate elements $300_A$–$300_N$ in collar assembly coupled together (via multiplexer 220) in a long range sensing modality switching unit so as to comprise the electrical equivalent of one large plate (having the effective surface area equivalent to the sum of the surface areas of the respective sensor plate elements in collar assembly 130).

As proximity sensing system 200 detects the presence of an object (due to the change in capacitance between the sensor plate elements and the patient), range sensing modality selector 251 generates signals to control multiplexer switching circuits 225 so as implement intermediate range sensing modality switching units. As multiple range sensing modality switching units are used, multiplexer 220 further is adapted to scan the respective sensing modality switching units (time multiplexing the capacitive sensing) so that objects in proximity to each of the respective sensing plate elements of the sensing modality switching units can be detected by processor 250. This processing enables both the accurate determination of ranges to objects at closer distances and also the localization of contour features of the patient 50, such as ears, nose, etc. so that control console 210 can generate appropriate command signals to the gantry arm actuators (e.g., electrical motors or the like) so as to ensure that collar assembly 125 is positioned at an optimal position with respect to the patient (without striking the patient). As collar assembly 130 and radiation detector assembly 125 are positioned increasingly closer to the patient, range sensing modality selector 251 commands progressively shorter range sensing modality switching units, perhaps down to the shortest range sensing modality switching unit comprising a single sensor plate element 300.

The shield feedback signal applied to shield plate elements 400 in each paired sensor-shield plate set effectively focuses the capacitive sensing of system 200 towards the patient so that the system is not affected by the capacitance that would otherwise be detected between the respective sensor plate elements 300 and the gantry arm components. Because patient 50 being imaged is relatively immobile for a given imaging session, the range signals generated by proximity detection system 200 can further be processed by imaging system 100 to provide a contour of a given patient and thus the system can "learn" a particular patient's profile and thereby facilitate faster imaging operation (e.g., positioning of the gantry arms) if progressive imaging procedures are required.

It will be apparent to those skilled in the art that, while the invention has been illustrated and described herein in accordance with the patent statutes, modifications and changes may be made in the disclosed embodiments without departing from the true spirit and scope of the invention. It is, therefore, to be understood that the appended claims are intended to cover all such modifications and changes as fall within the true spirit of the invention.

What is claimed is:

1. A capacitive proximity detection system for positioning a movable imaging element support structure with respect to a subject, the proximity detection system comprising:

a plurality of sensor plate elements disposed in a sensing pattern in a known spatial relationship with said movable imaging element support structure and further comprising a capacitive sensing processing unit;

a multiplexer coupled to said plurality of capacitive plate elements and adapted to selectively electrically couple said sensor element plates in one of a plurality of range sensing modality switching units, each of said range modality switching units comprising at least one of said sensor plate elements; and said capacitive sensing processing unit being coupled to said sensor plate elements via said multiplexer so as to generate an electric field around said sensor plates and detect proximity of objects to said sensor plates as a function of capacitance between said sensor plates and said subject so as to generate a range-to-subject signal for use in positioning said imaging element support structure.

2. The proximity detection system of claim 1 further comprising a shield system coupled to said multiplexer and comprising components disposed so as to focus capacitive sensing of said sensor plate elements away from said imaging element support structure and towards an imaging region.

3. The proximity detection system of claim 2 wherein said multiplexer comprises switching circuits adapted to selectively coupled said sensor plate elements together in at least a short range sensing modality switching unit and at least one long range sensing modality switching unit.

4. The proximity detection system of claim 3 wherein each short range modality switching unit comprises a single sensor plate element, and each modality switching unit other than said short range modality switching unit comprises at least two of said sensor plate elements.

5. The proximity detection system of claim 4 wherein said multiplexer switching circuits are further adapted to electrically couple respective ones of said sensor plates together for each modality switching unit other than said short range modality switching unit.

6. The proximity detection system of claim 1 wherein said capacitive sensing processor further comprises a range sensing modality selector for time multiplexing capacitance measurements from respective sensing modality switching units.

7. The proximity detection system of claim 2 wherein said shield system comprises a plurality of shielding plate elements and said capacitive sensing processor is coupled to said shielding plate elements to provide a guard plate feedback signal thereto corresponding to the sensed capacitance on said sensor plate elements.

8. The proximity detection system of claim 7 wherein the number of said plurality of shielding plate elements and the number of said plurality of sensor plate elements is the same.

9. The proximity detection system of claim 8 wherein said plurality of shielding plate elements are disposed between said plurality of sensor plate elements and said movable imaging element support structure, said shielding plate elements being disposed in a shielding pattern that corresponds with the sensor plates sensing pattern such that each sensor plate element is disposed in juxtaposition with a corresponding shielding plate element so as to form a plurality of paired sensor-shield plate sets.

10. The proximity detection system of claim 9 wherein said capacitive sensing processor comprises a respective attenuating feedback circuit for each sensor-guard plate set so as to generate said shield plate feedback signal.

11. The proximity detection system of claim 10 wherein each respective shield plate feedback signal corresponds to an attenuated sensed capacitance signal generated by said capacitive sensing system for the respective sensor plate element disposed in the respective sensor-shield plate set.

12. A radiation imaging system comprising:
a gantry arm having a radiation imaging system component mounted thereon, said gantry being movably coupled to a positioning device so as to dispose said radiation imaging system component in a selectable spaced relationship with respect to a subject;
a collar assembly disposed around said radiation imaging system component on said gantry arm;
a capacitive proximity detection system coupled to said positioning device so as to control the position thereof, the proximity detection system comprising:
a plurality of sensor plate elements disposed in said collar assembly in a sensing pattern in a known spatial relationship with said movable imaging element support structure;
a plurality of guard plate elements disposed in said collar assembly in a shielding pattern that corresponds to said sensing pattern so as to form a plurality of guard-sensor plate pairs;
a multiplexer coupled to said plurality of capacitive plate elements and adapted to selectively electrically couple said plates in one of a plurality of sensing range modalities;
a capacitive sensing processing unit coupled to said sensor plate elements via said multiplexer so as to generate an electric field around said sensor plates and detect proximity of objects to said sensor plates as a function of capacitance between said sensor plates and said subject; and
a shielding signal generation circuit coupled to said capacitive sensing system and to said multiplexer, said shielding generation circuit comprising a respective attenuating feedback circuit for each guard-sensor plate pair.

13. The radiation imaging system of claim 12 wherein said multiplexer comprises switching circuits for selectively electrically coupling respective ones of said sensor plate elements together in respective range modality switching units.

14. The radiation imaging system of claim 13 wherein said range modality switching units comprise a plurality of short range, intermediate range, and long range modality switching units, at least one short range modality switching unit each comprising a single sensor plate element, and at least one long range modality comprising all sensor plate elements disposed in said sensing pattern being coupled together.

15. The radiation imaging device of claim 12 wherein said collar assembly has a ring-like shape and said sensor plate elements are disposed at equiangular intervals around the circumference of said collar assembly.

16. The radiation imaging device of claim 15 wherein said sensor plate elements are disposed conformably on a first surface of said collar assembly, said first surface being disposed opposite the surface of said collar assembly in closest proximity to said gantry arm.

17. The radiation imaging device of claim 15 wherein said sensor plate elements and said guard plate elements comprising said guard-sensor plate pairs are disposed substantially parallel to one another within said collar assembly, said guard plate elements being disposed between said sensor plate elements and said gantry arm.

18. The radiation imaging device of claim 12 wherein said radiation imaging system component comprises an x-ray detection device.

* * * * *